United States Patent
Foppen et al.

(10) Patent No.: US 10,031,132 B2
(45) Date of Patent: Jul. 24, 2018

(54) MAGNETIC PARTICLE DETECTION WITH INCUBATION PERIOD

(71) Applicant: KONINKLIJKE PHILIPS N.V., Eindhoven (NL)

(72) Inventors: Sytske Foppen, Riethoven (NL); Bernardus Jozef Maria Beerling, Heeseijk-Dinther (NL); Willemina Maria Huijnen-Keur, Boxtel (NL); Hendrik Jan De Graaf, Eindhoven (NL); Danielle Walthera Maria Kemper-Van De Wiel, Eindhoven (NL); Roland Antonius Johannes Gerardus Smits, Breda (NL); Albert Hendrik Jan Immink, Eindhoven (NL); Femke Karina De Theije, Berghem (NL); Wendela Meertens, Eindhoven (NL)

(73) Assignee: Minicare B.V., Eindhoven (NL)

( * ) Notice: Subject to any disclaimer, the term of this patent is extended or adjusted under 35 U.S.C. 154(b) by 932 days.

(21) Appl. No.: 14/352,448

(22) PCT Filed: Oct. 5, 2012

(86) PCT No.: PCT/IB2012/055355
§ 371 (c)(1),
(2) Date: Apr. 17, 2014

(87) PCT Pub. No.: WO2013/057616
PCT Pub. Date: Apr. 25, 2013

(65) Prior Publication Data
US 2014/0329335 A1     Nov. 6, 2014

Related U.S. Application Data

(60) Provisional application No. 61/549,428, filed on Oct. 20, 2011.

(51) Int. Cl.
G01N 33/543 (2006.01)
B01L 3/00 (2006.01)
(Continued)

(52) U.S. Cl.
CPC .......... *G01N 33/543* (2013.01); *A61B 5/064* (2013.01); *A61B 5/113* (2013.01); *A61B 5/6805* (2013.01);
(Continued)

(58) Field of Classification Search
CPC .. G01N 33/543; G01N 35/0098; A61B 5/742; A61B 5/113; A61B 5/064; A61B 5/6805; B01L 3/502761
See application file for complete search history.

(56) References Cited

U.S. PATENT DOCUMENTS 7,425,455 B2    9/2008 Fukumoto et al.
2009/0251136 A1  10/2009 Prins et al.
(Continued)

FOREIGN PATENT DOCUMENTS

WO      2008142492 A1    11/2008
WO      WO2008142492     11/2008
(Continued)

OTHER PUBLICATIONS

R. Luxton et al., "Use of External Magnetic Fields to Reduce Reaction Times in an Immunoassay using Micrometer-Sized Paramagnetic Particles as Labels (Magnetoimmunoassay)", Anal. Chem. 2004, 76, pp. 1715-1719.

*Primary Examiner* — Melanie Yu Brown
(74) *Attorney, Agent, or Firm* — McCoy Russell LLP

(57) ABSTRACT

The invention relates to a method and a device for the detection of magnetic particles (1) in a sample chamber (112). After introduction of the sample into said sample chamber (112), the magnetic particles (1) are first retained
(Continued)

within the sample chamber (112) and kept away from the sensing surface (111) by an appropriate magnetic field (B) to allow for an incubation of the sample with reagents. A reference measurement may be made during this incubation period ($T_I$), preferably at the end thereof. After incubation, the magnetic particles (1) are allowed to contact the sensing surface (111) where a target measurement can be conducted.

14 Claims, 2 Drawing Sheets

(51) Int. Cl.
*A61B 5/06* (2006.01)
*A61B 5/113* (2006.01)
*A61B 5/00* (2006.01)
*G01N 35/00* (2006.01)

(52) U.S. Cl.
CPC ........ *A61B 5/742* (2013.01); B01L 3/502761 (2013.01); *B01L 2200/0668* (2013.01); *B01L 2300/0877* (2013.01); *B01L 2400/043* (2013.01); *B01L 2400/0487* (2013.01); *G01N 35/0098* (2013.01)

(56) References Cited

U.S. PATENT DOCUMENTS

| | | |
|---|---|---|
| 2010/0176798 A1 | 7/2010 | Van Lankvelt |
| 2010/0248345 A1* | 9/2010 | Luxton ................... B01L 99/00 435/287.1 |
| 2010/0297780 A1 | 11/2010 | De Theije et al. |
| 2011/0065209 A1* | 3/2011 | Heil ................. G01N 33/54326 436/501 |
| 2011/0114490 A1 | 5/2011 | Pamula et al. |
| 2011/0244596 A1 | 10/2011 | Evers et al. |
| 2012/0077184 A1* | 3/2012 | Hu ...................... B01L 3/50273 435/5 |
| 2013/0115715 A1* | 5/2013 | Hanning ............ G01N 21/4133 436/501 |

FOREIGN PATENT DOCUMENTS

| | | |
|---|---|---|
| WO | WO2008155723 | 12/2008 |
| WO | WO2010042242 | 4/2010 |
| WO | WO2010044007 | 4/2010 |
| WO | WO2011036634 | 3/2011 |
| WO | WO2011161499 | 12/2011 |

* cited by examiner

MAGNETIC PARTICLE DETECTION WITH INCUBATION PERIOD

CROSS-REFERENCE TO PRIOR APPLICATIONS

This application is the U.S. National Phase application under 35 U.S.C. § 371 of International Application Serial No. PCT/IB2012/055355, filed on Oct. 5, 2012, which claims the benefit of U.S. Application Ser. No. 61/549,428, filed on Oct. 20, 2011. These applications are hereby incorporated by reference herein.

FIELD OF THE INVENTION

The invention relates to a method and a sensor device for the detection of magnetic particles at the sensing surface of a sample chamber.

BACKGROUND OF THE INVENTION

WO 2010/044007 A2 discloses a procedure in which magnets above and below a reaction chamber are used to generate an alternating magnetic field that moves magnetic particles in the reaction chamber to a sensor surface. A problem may occur in this and similar approaches when the sample has to be contacted with reagents at the beginning of an assay, because non-stationary conditions prevent accurate and reproducible measurements during such an incubation period.

SUMMARY OF THE INVENTION

It is an object of the invention to provide means for an improved detection of magnetic particles in a sample during an assay that requires an incubation of the sample with reagents.

This object is achieved by methods according to claims 1 and 2 and a sensor device according to claim 3. Preferred embodiments are disclosed in the dependent claims.

A method according to the present invention comprises the detection of magnetic particles at a sensing surface of a sample chamber.

In this context, the term "magnetic particles" shall comprise both permanently magnetic particles as well as magnetizable particles, for example superparamagnetic beads. The size of the magnetic particles typically ranges between 3 nm and 50 µm. Moreover, the magnetic particles may comprise bound target components one is actually interested in. The "sample chamber" is typically an open cavity, a closed cavity, or a cavity connected to other cavities by fluid connection channels. The "sensing surface" of the sample chamber is just one dedicated interior (piece of) surface of this chamber at which a detection of magnetic particles or other entities can take place by an appropriate method. The sensing surface will often be provided with binding sites at which magnetic particles can specifically bind.

The method comprises the following steps:

Introducing a sample into the sample chamber. The sample will typically be a fluid, for example a body liquid like blood or saliva. Introduction of such a fluid into the sample chamber may take place actively, using for example some pumping mechanism, or passively via capillary forces.

Incubating the aforementioned sample for an incubation period with reagents comprising magnetic particles. The incubation period typically starts immediately after the introduction of the sample into the sample chamber. It should last long enough for a sufficient mixing and (if applicable) reaction between sample and reagents.

Retaining the magnetic particles within the sample chamber during the aforementioned incubation period while at the same time keeping the magnetic particles away from the sensing surface by a magnetic field.

It should be noted that the aforementioned "retaining" and "keeping away" can usually not perfectly be achieved on a microscopic scale. Hence the statement is to be understood in the sense that more than 90%, preferably more than 99% of the magnetic particles are retained in the sample chamber and/or kept away from the sensing surface during the incubation period.

Moreover, the retention of the magnetic particles within the sample chamber typically comprises that they are distributed across the whole sample chamber besides a region adjacent to the sensing surface. Typically, this "forbidden" region has a size of 50% of the chamber volume extending perpendicular from the sensing surface, preferably 10% perpendicular from the sensing surface, or most preferred about 2% of the total size of the sample chamber perpendicular to the sensing surface. The invention shall however also comprise the application of a magnetic field which restricts the location of the magnetic particles during the incubation period to a fixed volume, for example in an incubation region of the sample chamber.

According to another aspect, the invention relates to a sensor device for the detection of magnetic particles at the sensing surface of a sample chamber, said sensor device comprising the following components:

A magnetic field generator for generating a magnetic field in the sample chamber. The magnetic field generator may for example comprise one or more permanent magnets and/or electromagnets.

A control unit for controlling the magnetic field generator such that the generated magnetic field retains magnetic particles in the sample chamber while keeping them away from the sensing surface, wherein this control may particularly take place during an incubation period during which a sample is incubated with reagents comprising magnetic particles. The control unit may be realized by dedicated electronic hardware, digital data processing hardware with associated software, or a mixture of both.

The methods and the sensor device are different realizations of the same inventive concept, i.e. the retention of magnetic particles from a sensing surface during an incubation period. Explanations and definitions provided for one of these realizations are therefore valid for the other realization, too. The methods and the sensor device have the advantage that the sensing surface is not "contaminated" by magnetic particles until the incubation period is over, which can considerably improve the accuracy of the measurement results. Moreover, retention of the magnetic particles within the sample chamber guarantees that they cannot be washed away by uncontrolled fluid movements, in which case they would be lost.

In the following, various preferred embodiments of the invention will be described that relate to both the methods and the sensor device described above.

According to a first preferred embodiment, a measurement is made at the sensing surface during the incubation period. This measurement is called "reference measurement" in the following because it relates to a situation in which the sample (and possible reagents not comprising magnetic particles) can already contact the sensing surface while magnetic particles cannot, which may serve as a reference for (later) measurements during which magnetic particles contact or even bind to the sensing surface. It is a particular advantage of the present invention that such a reference measurement can be made while it is guaranteed that no magnetic particles are at the sensing surface.

The aforementioned reference measurement is preferably made closer to the end of the incubation period than to its beginning, because the conditions in the sample chamber are then more stationary and reproducible. In particular, at least a part of the reference measurement is preferably made after about 70% of the incubation period, most preferably after about 90% of the incubation period.

Typical values for the duration of the incubation period range between about 10 s and 900 s, preferably between about 10 s and about 200 s.

It was already indicated that in many cases a measurement is made at the sensing surface after the incubation period is over. Such a measurement will in the following be called "target measurement" because it typically yields the signal one is actually interested in, for example a signal related to be presence and/or amount of a certain target substance in the sample. The evaluation of the target measurement may preferably make use of the above-mentioned reference measurement.

The reference measurement and/or the target measurement may in general be made with any suited sensing modality. Preferably, an optical sensor unit is provided for conducting an optical detection at the sensing surface, particular for the detection of light originating from a frustrated total internal reflection (FTIR) of a light beam at the sensing surface. FTIR is a detection technique that is surface specific and therefore particularly suited in the context of the present invention.

While the magnetic particles are kept away from the sensing surface during the incubation period, they are usually wanted there after incubation has been accomplished. To accelerate the migration of the magnetic particles to the sensing surface, they may preferably be actuated towards the sensing surface after the incubation period. This actuation may particularly be done with the help of a suitable magnetic field (with a nonzero gradient) exerting magnetic forces on the magnetic particles.

During the incubation period, the magnetic particles are preferably kept away from the sensing surface a distance of at least about 4 μm, more preferably of at least about 10 μm, most preferably of at least about 100 μm. Thus it can be guaranteed that they cannot interfere with typical surface specific detection techniques (e.g. FTIR).

The magnetic field that is applied during the incubation period may preferably be modulated. In particular, the magnetic field and/or and its gradient may repetitively change direction. In this case the mechanical actuation of the magnetic particles is modulated accordingly, allowing for example for an improved mixing with the sample.

The sample chamber with the sensing surface may be an integral component of the sensor device. According to a preferred embodiment, the sample chamber is however provided in a cartridge which is a component of its own (distinct from the sensor device). Such a cartridge is typically a disposable device that can be discarded after one use.

The sample chamber is preferably equipped with reagents before its use, i.e. before a sample is introduced and incubation starts. The reagents may particularly be provided in dried form, optionally covered by some protective layer (e.g. sucrose). All that has to be done to start an assay in such a prepared sample chamber is the introduction of the sample to be investigated.

BRIEF DESCRIPTION OF THE DRAWINGS

These and other aspects of the invention will be apparent from and elucidated with reference to the embodiments described hereinafter.

In the drawings.

Like reference numbers refer in the Figures to identical or similar components.

DETAILED DESCRIPTION OF EMBODIMENTS

Figure 1:
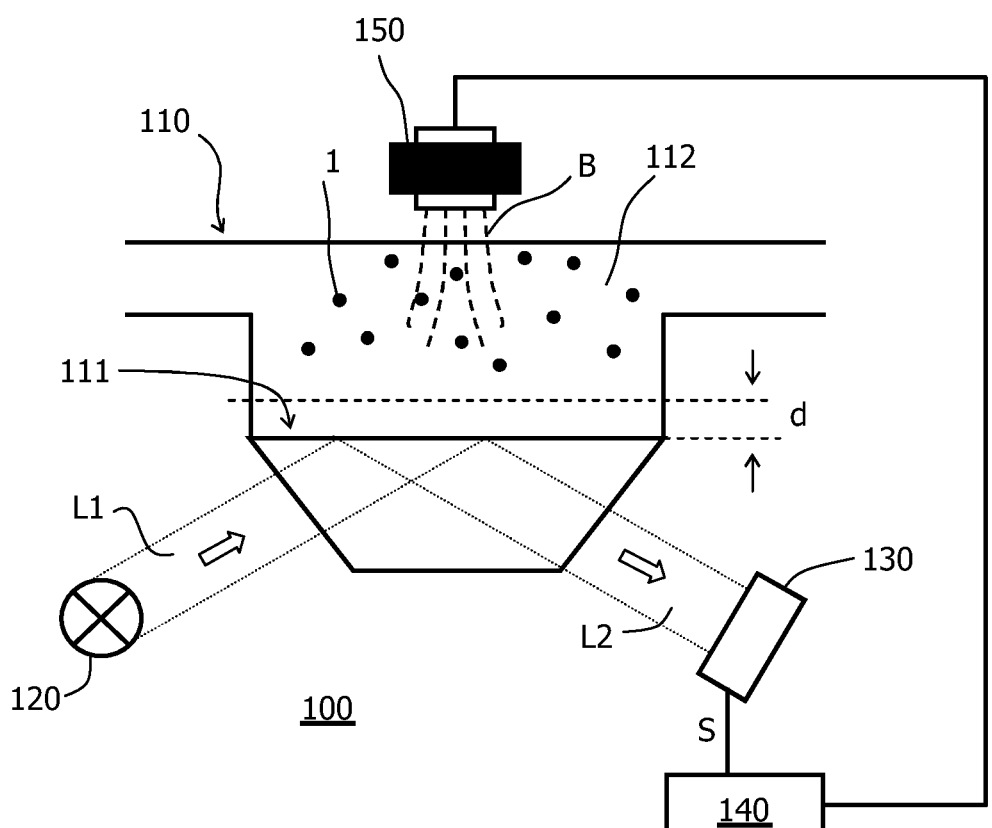
FIG. 1 shows a schematic side view of a sensor device according to the present invention.

FIG. 1 shows a biosensor device 100 according to the invention in a schematic side view. The sensor device 100 is designed to make optical measurements in a disposable cartridge 110 in which a sample with target components of interest can be provided. The cartridge 110 may for example be made from glass or transparent plastic like poly-styrene. It comprises a sample chamber 112 in which a sample fluid with target components to be detected (e.g. drugs, antibodies, DNA, parathyroid hormone PTH etc.) can be provided. The sample further comprises magnetic particles 1, for example superparamagnetic beads (typical diameter: 500 nm), wherein these particles 1 are usually bound as labels to the aforementioned target components (for simplicity only the magnetic particles 1 are shown in the Figure).

The cartridge 110 has a transparent bottom with a "sensing surface" 111 that (partially) borders the sample chamber 112. A plurality of "detection spots" are typically disposed on the sensing surface 111. They comprise binding sites, e.g. antibodies, which can specifically bind the target components.

The sensor device 100 comprises a light source 120 for emitting an "input light beam" L1, a light detector 130 for detecting and measuring an "output light beam" L2, and an evaluation unit 140 for evaluating the signals S of the light detector. The input light beam L1 generated by the light source 120 arrives at the sensing surface 111 at an angle larger than the critical angle of total internal reflection (TIR) and is therefore totally internally reflected as the output light beam L2. The output light beam L2 leaves the cartridge 110 and is detected by the light detector, e. g. by the light-sensitive pixels of a camera 130. The light detector 130 thus generates an image of the sensing surface, which is further processed in the evaluation unit 140.

The sensor device 100 further comprises a magnetic field generator, for example realized by electromagnets 150 with a coil and a core disposed at the bottom (not shown) and/or at the top of the cartridge 110, for controllably generating a magnetic field B in the sample chamber 112. With the help of this magnetic field, the magnetic particles 1 can be manipulated, i.e. be magnetized and particularly be moved (if magnetic fields with gradients are used). Thus it is for example possible to attract magnetic particles 1 to the sensing surface 111 in order to accelerate the binding of the associated target component to said surface.

The described sensor device 100 applies optical means for the detection of magnetic particles 1 at the sensing surface 111. For eliminating or at least minimizing the influence of background (e.g. of the sample fluid, such as saliva, blood, etc.), the detection technique should be surface-specific. As indicated above, this is achieved by using the principle of frustrated total internal reflection. This principle is based on the fact that an evanescent wave propagates (exponentially dropping) into the sample chamber 112 when the incident light beam L1 is totally internally reflected. If this evanescent wave then interacts with another medium having a different refractive index from water like the magnetic particles 1, part of the input light will be coupled into the sample fluid (this is called "frustrated total internal reflection"), and the reflected intensity will be reduced (while the reflected intensity will be 100% for a clean interface and no interaction). Further details of this procedure may be found in the WO 2008/155723 A1, which is incorporated into the present text by reference.

The magnetic particles 1 and optional other reagents that are needed for an assay are preferably stored beforehand in dried form in the sample chamber 111 of the cartridge 110. An assay with the described sensor device 100 and cartridge 110 then starts with the introduction of a sample fluid into the sample chamber 112. After wetting of the sample chamber 112 with dried reagents, the reagents start to dissolve and uncontrolled fluid flows and diffusion can exist which may move the reagents away from the reaction volume. Furthermore, the magnetic beads 1 may reach the sensing surface 111 too early and already bind to it, i.e. before a good reference measurement of the sensing surface can be performed.

In order to address the aforementioned problems, it is proposed here to keep the magnetic beads 1 in the sample chamber 112 while keeping them away from the sensing surface 111. In this way a proper reference measurement can be done on the sensing surface without interference of the magnetic beads. Keeping the magnetic beads in the appropriate position in the sample chamber can be achieved by using magnetic attraction by magnets near the sample chamber. Thus a layer of thickness d adjacent to the sensing surface 111 can (macroscopically) be kept free of magnetic particles 1, wherein d typically ranges between about 1 μm and 1000 μm.

Figure 2:
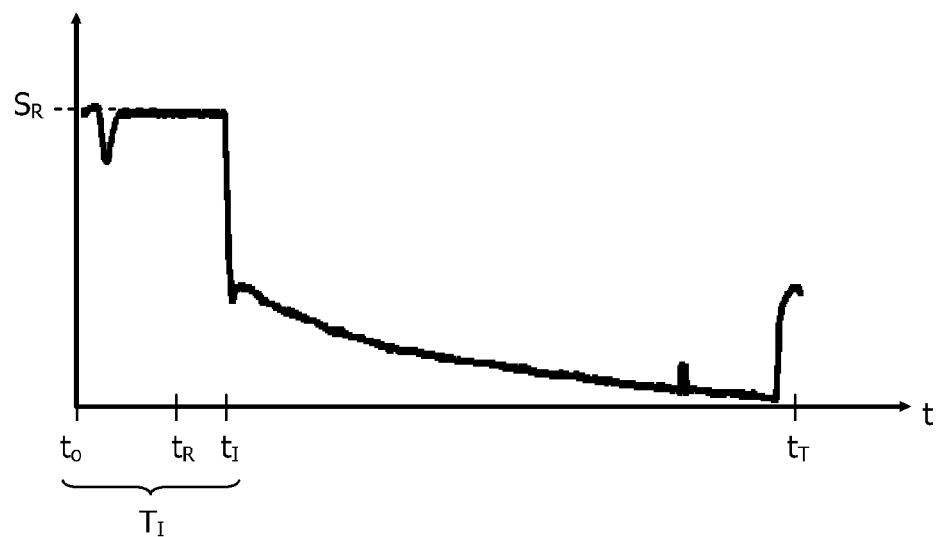
FIG. 2 shows an exemplary course of the sensing signal in the sensor device of FIG. 1.

FIG. 2 shows schematically an exemplary course of sensor signals S as they may be generated with the sensor device 100 of FIG. 1. At a time $t_0$, the sample is introduced into the sample chamber 112. Wetting of the sensing surface 111 and mixing of the sample with the dried reagents causes an increase of the detection signal S that typically is initially irregular. At a second time $t_I$, the incubation of the sample with reagents is completed. The time interval $T_I=(t_I-t_0)$ hence corresponds to the required "incubation period" of the assay.

When the invention is used, a low (or even zero) background signal level of beads on the sensing surface is observed during the total incubation period. During the incubation period the bulk incubation takes place but only limited or no binding of magnetic particles to the sensing surface occurs. So the time point for a reference measurement at the sensing surface can be taken during the whole incubation period $T_I$ (in contrast to the conventional situation, in which reference measurements are done before or at the beginning of the incubation period to avoid interferences with beads).

In practice it is often observed that dark spots appear in the cartridge some seconds after wetting, due to dissolving of the reagents (sucrose and proteins). These dark spots are unwanted when a reference measurement is done.

A reference is therefore preferably taken at the end of the incubation (after the dark spots have disappeared) instead of at the beginning. This is advantageous as the conditions in the sample chamber are more stationary at the end of the incubation period $T_I$. This is indicated in FIG. 2 by the time point $t_R$, at which the reference signal $S_R$ is measured at the sensing surface. A reference time point of $t_R=85$ s may for example be chosen when the incubation starts at $t_0=0$ and ends at $t_I=95$ s (at which optical detection must be completed) and the reference duration for optical detection is 4.8 s (at 25 FPS). This late reference allows more time for the operator to follow the defined workflow.

After the end of the incubation period, the magnetic beads 1 are allowed to migrate to the sensing surface or even actively moved towards it. The latter may for example be achieved with a magnet appropriately disposed below the sensing surface 111 (not shown in FIG. 1). At a time point $t_T$, one or more "target" measurements can be made at the sensing surface, showing the amount of magnetic particles 1 that have specifically bound to the sensing surface. This measurement value can then be evaluated by taking the reference value $S_R$ into account (e.g. as an offset, a normalization factor or the like). The magnetic field during (and/or after) the incubation period is preferably applied in a pulsed manner to mix the sample fluid with the magnetic beads and enhance incubation (i.e. to perform an "active incubation"). When using the magnets in a pulsed manner, incubation of magnetic beads with target molecules can be enhanced due to active mixing. Thus the eventual signal change can be increased and the cartridge-to-cartridge variation can be decreased, due to keeping more beads in the sample chamber and mixing of the beads and fluid. Such an "active incubation" can be used in any immuno-assay which makes use of magnetic beads.

Figure 3:
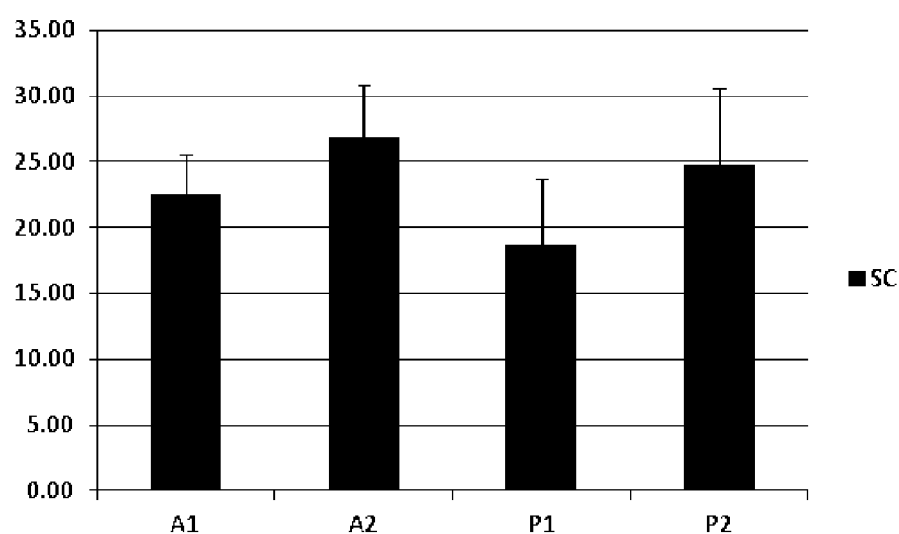
FIG. 3 shows measurement data obtained for samples that were actively and passively actuated, respectively.

FIG. 3 shows measurement results obtained for the proposed "active incubation" (indicated by a letter "A") and for the conventional "passive incubation" (indicated by a letter "P"). In these results it can be seen that the "active incubation" has a positive effect both on the signal and on the standard deviation, due to the higher amount of beads retained in the reaction volume, the lower signal on the reference measurement, and the reproducibility due to the retention of the beads.

In summary, the invention proposes to use magnets placed near (e.g. above) a sample chamber during the incubation phase, i.e. when the sample enters the sample chamber and comes into contact with the dried reagents. This keeps the magnetic beads 1) away from escaping the sample chamber and 2) away from the sensing surface of this chamber.

By keeping the magnetic beads away from escaping the reaction chamber, a clear increase in signal change is observed and the cartridge-to-cartridge variation is significantly reduced. By keeping the magnetic beads away from the sensing surface of this chamber, a proper reference measurement can be done on the sensing surface without interference of the magnetic beads.

An important element of the invention is using magnets near a reaction chamber to keep the magnetic beads in the right position of the chamber so that a reference measurement can be performed. An additional use is by using the magnets pulsated the incubation can be enhanced by active mixing (i.e. active incubation).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method comprising the detection of magnetic particles at a sensing surface of a sample chamber, wherein said sample chamber is equipped with reagents before a sample is introduced, said method further comprising:
   introducing a sample into the sample chamber;
   incubating said sample for an incubation period ($T_I$) with reagents comprising magnetic particles;
   retaining said magnetic particles within the sample chamber during the incubation period ($T_I$) while keeping them away from the sensing surface by a modulated magnetic field (B);
   conducting a reference measurement at the sensing surface during the incubation period ($T_I$) after about 70% of the incubation period ($T_I$).

2. A sensor device for the detection of magnetic particles at a sensing surface of a sample chamber, comprising:
   a magnetic field generator for generating a magnetic field (B) in the sample chamber;
   a control unit comprising instructions to control said magnetic field (B) to retain magnetic particles in the sample chamber while keeping the magnetic particles away from the sensing surface during an incubation period ($T_I$), wherein a reference measurement ($t_R$, $S_R$) is made at the sensing surface during the incubation period, and
   wherein reagents are disposed in the sample chamber before a sample is introduced.

3. The sensor device according to claim 2, wherein at least a part of the reference measurement ($t_R$, $S_R$) is made after about at least 20% of the incubation period ($T_I$).

4. The sensor device according to claim 2, wherein the incubation period ($T_I$) lasts between about 10 s and about 900 s.

5. The sensor device according to claim 2, wherein a target measurement ($t_T$) is made at the sensing surface after the incubation period ($T_I$).

6. The sensor device according to claim 2, wherein a sensor unit is provided for conducting an optical detection at the sensing surface, particular for the detection of a frustrated total internal reflection of a light beam (L1) at the sensing surface.

7. The sensor device according to claim 2, wherein the magnetic particles are actuated towards the sensing surface after the incubation period ($T_I$).

8. The sensor device according to claim 2, wherein, during the incubation period ($T_I$), the magnetic particles are disposed a distance (d) of at least approximately 10 μm from the sensing surface.

9. The sensor device according to claim 2, wherein the magnetic field (B) is modulated during the incubation period ($T_I$).

10. The sensor device according to claim 2, wherein the magnetic field (B) and/or its gradient repetitively changes direction during the incubation period ($T_I$).

11. The sensor device according to claim 2, wherein the sample chamber is provided in a cartridge.

12. The sensor device according to claim 2, wherein at least a part of the reference measurement ($t_R$, $S_R$) is made after approximately 70% of the incubation period ($T_I$).

13. The sensor device according to claim 2, wherein, during the incubation period ($T_I$), the magnetic particles are disposed a distance (d) of at least approximately 100 μm from the sensing surface.

14. The sensor device according to claim 2, wherein, during the incubation period ($T_I$), the magnetic particles are disposed a distance (d) in a range of approximately 1 μm and approximately 1000 μm.

* * * * *